United States Patent [19]

Hidaka et al.

[11] Patent Number: 4,871,867

[45] Date of Patent: Oct. 3, 1989

[54] PROCESS FOR PRODUCING A POLYGLYCIDYLAMINO COMPOUND

[75] Inventors: Toshio Hidaka, Hiratsuka, Japan; Tetsuo Mizuno, Forest Hills, N.Y.

[73] Assignee: Mitsubishi Gas Chemical Company, Inc., Tokyo, Japan

[21] Appl. No.: 176,180

[22] Filed: Mar. 31, 1988

[30] Foreign Application Priority Data

Apr. 3, 1987 [JP] Japan ................................. 62-81050

[51] Int. Cl.$^4$ ........................................... C07D 301/27
[52] U.S. Cl. ..................................................... 549/514
[58] Field of Search ........................................ 549/514

[56] References Cited

U.S. PATENT DOCUMENTS 3,683,044  8/1972  Huang et al. ...................... 549/514

FOREIGN PATENT DOCUMENTS 114981  5/1987  Japan ................................. 549/514

OTHER PUBLICATIONS

Chemical Abstracts, vol. 102 (No. 15) (Apr. 15, 1985).

*Primary Examiner*—Mary C. Lee
*Assistant Examiner*—Robert C. Whittenbaugh
*Attorney, Agent, or Firm*—Wenderoth, Lind & Ponack

[57] ABSTRACT

Process for producing a polyglycidylamino compound characterized by comprising:

(I) an addition reaction step at which a diamine is reacted with an excess amount, based on diamine, of an epihalohydrin in the presence of water, (II) a primary dehydrohalogenatin reaction step at which the addition reaction mixture from the step (I) is reacted with a halogen-removing agent in the co-presence of at least one phase transfer catalyst, (III) a step at which the dehydrohalogenation reaction mixture from the step (II) is separated into an organic phase and a water phase by adding water thereto, and an unreacted epihalohydrin is distilled off from the organic phase, (IV) a step at which the reaction mixture from the step (II) is washed with water, (V) a secondary dehydrohalogenation reaction step at which the crude polyglycidylamino compound from the step (IV) is reacted with a halogen-removing agent in the co-presence of at least one phase transfer catalyst, and (VI) a step at which the dehydrohalogenation reaction mixture from the step (V) is washed with water.

16 Claims, No Drawings

PROCESS FOR PRODUCING A POLYGLYCIDYLAMINO COMPOUND

FIELD OF THE INVENTION

This invention relates to a process for producing a polyglycidylamino compound from diamine and epihalohydrine, and especially, it relates to a process for producing a high quality polyglycidylamino compound which has a very low halogen content, low viscosity, excellent storage stability and light color.

PRIOR ARTS OF THE INVENTION

For example, Japanese Patent Publication Nos. 6828/1986 and 7198/1986 already discloses a process for producing polyglycidylamino compounds represented by general formula (1)

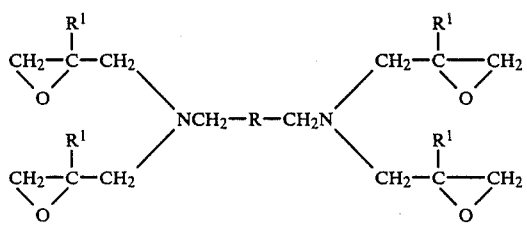

wherein R represents a phenylene group or cyclohexylene group and $R^1$ represents a hydrogen atom or methyl group, by reacting a diamine represented by general formula (2)

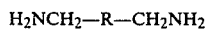

wherein
R is as defined above
with an epihalohydrin represented by general formula (3)

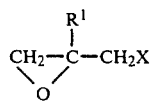

wherein $R^1$ is as defined above and X represents a chlorine or bromine atom, and then effecting dehydrohalogenation of the reaction product.

The above process makes it possible to produce the corresponding polyglycidylamino compounds on an industrial scale.

In the process of Japanese Patent Publication No. 6828/1986, a diamine and epihalohydrin are reacted, and then the dihydrohalogenation reaction is carried out with removing water from the reaction system while alkali is being added to the reaction mixture, to produce a polyglycidylamino compound.

The process of Japanese Patent Publication No. 7198/1986 comprises reacting a diamine and epihalohydrin, then carrying out the dehydrohalogenation reaction of the reaction mixture with removing water from the system while alkali is being added or after alkali has been added, dissolving the resulting polyglycidylamino compound in an organic solvent to form an organic layer and a solid substance, and distilling off a volatile component from the organic layer, to produce a polyglycidylamino compound.

Polyglycidylamino compounds obtained in the above processes has a low viscosity and excellent processability, and are useful as epoxy resins which give cured resin excellent in heat resistance, adhesion, stiffness, mechanical strengths, etc. By utilizing these characteristics, the above polyglycidylamino compounds are used in various applications such as casting material, matrix for carbon fiber composite, structural material in aerospace and aircraft industries, material for electric and electronic parts, articles for sports, crosslinking agent, etc.

In recent years, however, the technical field of electonics has a strong desire for epoxy resins in which the halogen content is decreased as much as possible. However, the residual content of hydrolyzable halogen is relatively large in polyglycidylamino compounds obtained by the above-mentioned conventional process. And it is usual that the residual content is 1000 ppm or more, and whatever modification may be added to the procedures of the above conventional process, it has been difficult to decrease the content of hydrolyzable halogen to below some hundreds ppm.

Further, a considerable amount of non-hydrolyzable halogen is also present in polyglycidylamino compounds obtained in the above conventional process. The presence of these residual non-hydrolyzable halogen and hydrolyzable halogen causes fatal defects such as degradation of a substrate, corrosion of metal, etc., especially when the so-produced polyglycidylamino compounds are used in the field of electronics.

Therefore, it has been seriously desired to develop a technology which makes it possible to produce polyglycidylamino compound in which the halogen content is reduced as much as possible.

SUMMARY OF THE INVENTION

It is an object of this invention to provide a polyglycidylamino compound suitable for the production of an epoxy resin free from degradation of a substrate and corrosion of a metal.

It is another object of this invention to provide a polyglycidylamino compound having a low halogen content.

It is yet another object of this invention to provide a polyglycidylamino compound having a reduced content of hydrolyzable halogen.

This invention provides a process for producing a polyglycidylamino compounds represented by general formula (1)

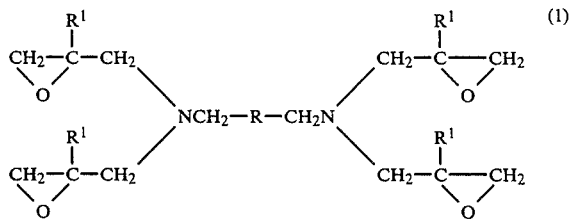

wherein R represents a phenylene group or cyclohexylene group and $R^1$ represents a hydrogen atom or methyl group,
by reacting a diamine represented by general formula (2)

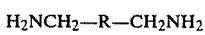

wherein R is as defined above,
with an epihalohydrin represented by general formula (3)

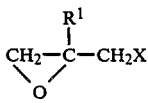
(3)

wherein $R^1$ is as defined above, and X represents a chlorine or bromine atom,
and then carrying out a dehydrohalogenation reaction of the reaction mixture; said process for producing a polyglycidylamino compound characterized by comprising:

(I) an addition reaction step at which a diamine is reacted with an excess amount, based on diamine, of an epihalohydrin in the presence of water, (II) a primary dehydrohalogenation reaction step at which the addition reaction mixture from the step (I) is reacted with a halogen-removing agent in the co-presence of at least one phase transfer catalyst, (III) a step at which the dehydrohalogenation reaction mixture from the step (II) is separated into an organic phase and a water phase by adding water thereto, and an unreacted epihalohydrin is distilled off from the organic phase, (III) a step at which the reaction mixture from the step (III) is washed with water, (V) a secondary dehydrohalogenation reaction step at which the crude polyglycidylamino compound from the step (IV) is reacted with a halogen-removing agent in the co-presence of at least one phase transfer catalyst, and (VI) a step at which the dehydrohalogenation reaction mixture from the step (IV) is washed with water.

DETAILED DESCRIPTION OF THE INVENTION

This invention has been completed based on the finding that the desired polyglycidylamino compound having a low halogen content can be obtained by devising the dehydrohalogenation reaction of a halohydrin compound obtained by adding epihalohydrin to diamine.

In the essential steps (II) and (V) of the process of this invention, the halogen removing agent promotes the dehydrohalogenation reaction very effectively owing to the catalytic action of the phase transfer catalyst.

Examples of the halogen-removing agent used in these steps include alkali metal or alkali earth metal hydroxide, inorganic acid salt of alkali metal or alkali earth metal carbonate, sulfite, thiosulfate, phosphite or thiocyanate; alkali metal or alkali earth metal salt of aliphatic or aromatic carboxylic acid having a carbon number of 1 to 12, typified by potassium acetate, sodium oxalate, potassium benzoate, etc.; alkali metal alkoxide of aliphatic alcohol having a carbon number of 1 to 10, typified by sodium methoxide, sodium ethoxide, potassium t-butoxide, etc.; and alkali metal phenoxide typified by sodium phenoxide, etc. In these compounds, alkali metal hydroxide, alkali metal salt of inorganic acid, alkali metal salt of carbonic acid and alkali metal alkoxide are preferable. Further, alkali metal hydroxide, alkali metal salt of inorganic acid and alkali metal alkoxide are more preferable, and especially, alkali metal alkoxide is most preferable. Two or more of these halogen-removing agents may be used in combination as required. It is preferable to include alkali metal hydroxide, alkali metal salt of inorganic acid or alkali metal alkoxide in the combination, and in particular, alkali metal hydroxide is most preferably used in the combination. In particular, a combination of the above hydroxide with sulfite or phosphite is effective.

The phase transfer catalyst in this invention is capable of solubilizing or extacting halogen-removing agent, in the form of ion pairs, into organic phase.

Examples of the phase transfer catalyst are compounds of the following groups 1 to 4.

Group 1: onium salt compounds.

Group 2: macrocyclic polyether compounds such as crown ethers and cryptands,

Group 3: linear polyether compounds such as polyalkylene oxides and their derivatives having alkyletherified terminls and polyethear amines.

Group 4: aprotic polar compounds.

From the industrial viewpoint, Groups 1, 3 and 4 are preferably used, more preferably used are Groups 1 and 4, and most preferably Group 1. The compounds of Groups 1 to 4 may be used in combination. A combination of Group 1 with the other Group(s) and a combination of Group 4 with the other Group(s) are desirable, and especially, combinations of Group 1 with Group 4 and Group 3 with Group 4 are more desirable.

Examples of the above Group 1 compounds specifically include quaternary ammonium salts such as tetramethyl ammonium chloride, tetrabutyl ammonium chloride, benzyltriethyl ammonium chloride, methyltrioctyl ammonium chloride, N-laurylpicolinium chloride, etc.; quaternary phosphonium salts such as tetramethyl phosphonium chloride, tetraethyl phosphonium chloride, tetrabutyl phosphonium bromide, tribenzylethyl phosphonium chloride, tributylethyl phosphonium chloride, etc.; and tertiary sulfonium salts such as trimethyl sulfonium iodide, dibenzylmethyl sulfonium bromide, etc. The number of carbons in these compounds is preferably 8 to 16, more preferably 12 to 16. Of these compounds for Group 1, preferably used are ammonium salt and phosphonium salt, and especially, ammonium salt is preferably used.

Examples of the above Group 2 compounds specifically include crown ethers such as 12-crown-4, 15-crown-5, benzo-15-crown-5, 18-crown-6, dibenzo-18-crown-6, dicyclohexyl-18-crown-6, dibenzopyridino-18-crown-6, dibenzo-24-crown-8, etc., and cryptands such as diaza-15-crown, diaza-18-crown, [2,2,2]-cryptand, [2,2,1]-cryptand, [2,1,1]-cryptand, [2,2,2]-decylcryptand, [2,2,2]-benzocryptand, Kryptfix 222B polymer, Kryptfix 221B polymer ("Kryptfix" is a product name of cryptand manufactured by Merk Co.). Of these compounds, preferably used are 12 to 24-membered crown ethers and cryptands, and particularly preferably used are 12-crown-4, 15-crown-5, 18-crown-5, dibenzo-18-crown-6 and dibenzo-24-crown-8.

Examples of the above Group 3 compounds include polyalkylene oxides and their terminally alkyleterified products such as polyethylene glycol, polyethylene glycol dimethyl ether, polyoxypropylene glycol, polyoxypropylene glycol dimethyl ether, etc., and polyether amines such as tris(3,6-dioxaheptyl) amine. Of these compounds, preferably used is polyalkylene oxide, and especially preferably used is polyethylene glycol.

Examples of the above Group 4 compounds include those compounds known as solvents aprotic polar solvent, such as hexamethyl phosphoric acid triamide, dimethyl sulfoxide, dimethyl formaldehyde, dimethyl acetamide, acetonitrile, N-methyl pyrrolidone, etc. Of these compounds, especially preferably used are hexamethyl phosphoric acid triamide and dimethyl sulfoxide.

The process of this invention is carried out in the following procedures.

First, at the step (I), a diamine of formula (2) is reacted with an epihalohydrin of formula (3) to form an addition product, i.e., a halohydrin compound. Examples of the diamine used at this step may be m-xylylene diamine, p-xylylene diamine, a mixture of these, 1,3-bisaminomethylcyclohexane, 1,4-bisaminomethylcyclohexane, a mixture of these, etc. Examples of the epihalohydrin may be epichlorohydrin, epibromohydrin and β-methylepichlorohydrin, and in general epichlorohydrin is used.

Epihalohydrin is used stoichiometrically in an excess amount to diamine, and usually it is used in an amount in the range from 5.5 to 15 moles per mole of diamine. Water, which has to be present in the addition reaction system, contributes to promotion of addition reaction and prevention of precipitation of crystalline substances, and is used in an amount in the range from 0.5 to 15 moles per mole of diamine. The addition reaction here is an exothermic one. In general, therefore, diamine is added to a mixture system of epihalohydrin and water by slow degrees to control the reaction such that the temperature of the reaction system does not exceed 60° C.

Then, at the step (II), the reaction mixture obtained at the step (I) is subjected to a dehydrohalogenation reaction in which it is reacted with a halogen-removing agent. The phase transfer catalyst used at this step (II) has an action on the halogen-removing agent to render the halogen-removing agent soluble in the organic phase, and promotes the dehydrohalogenation reaction. The phase transfer catalyst exhibits a remarkable activity; it greatly contributes to prevention of side reaction and accomplishment of the main reaction as compared with conventional dehydrohalogenation reactions usually carried out by using alkali alone, and as a result, the halogen content in the resulting product is reduced. With regard to the amount of the halogen-removing agent to be used at the step (II), it is usual practice to select an amount larger than the stoichiometric amount of 4 moles per mole of diamine as a material. Since, however, the use of too large an amount of said agent destroys the resultant epoxy groups, it is general practice to select the amount in the range not exceeding 5 moles. The amount of the phase transfer catalyst may be so-called a catalytic amount, and usually, said amount may be selected from the range from $10^{-4}$ to $10^{-1}$ mole per mole of diamine as a material. In the case of using a halogen-removing agent, reaction of which is prevented by a water content in the reaction system, such as metal alkoxide, it is necessary to fully remove the water content in the reaction system after the step (I), however, the water content does not cause a trouble if it is very small. In the primary dehydrohalogenation reaction at the step (II), it is preferable to maintain the reaction at a temperature not exceeding 70° C., usually, at a temperature of 20° to 50° C.

At the step (III), water is added to the reaction mixture resulting from the step (II) to separate into a water phase and an organic phase, and remove the water phase containing metal halide formed by the dehydrohalogenation reaction, and excessive epihalohydrin is distilled off from the resulting organic phase obtained by separation.

Then, at the step (IV), the reaction mixture obtained by distilling off the excessive epihalohydrin is subjected to a washing step. Usually, at this washing step, the reaction mixture is dissolved in an organic solvent. The solvent used here is compatible with and inert to the end product, polyglycidylamino compound, and it is substantially not compatible with water. Specifically, aromatic hydrocarbons such as benzene, toluene, xylene, etc., are preferably used. The amount of the solvent used is 30 to 500 parts by weight, preferably 50 to 300 parts by weight, per 100 parts by weight of the polyglycidylamino compound.

The amount of water used at the washing step (IV) is 10 to 200 parts by weight, preferably 20 to 100 parts by weight, per 100 parts by weight of the polyglycidylamino compound. Naturally, the washing effect further improves if the washing is carried out twice or more.

The above washing step to be carried out after distilling off an excess amount of epihalohydrin from the reaction mixture at the step (II) is effective to separate and remove epihalohydrin which can not be completely removed by said distilling-off. This washing step not only makes it possible to proceed smoothly with the secondary dehydrohalogenation reaction at the next step, but also prevents the coloring of an end product, improves the storage stability thereof, and contributes to reduction of the halogen content. Thus, this washing step is indispensable.

The reaction mixture from the washing step (IV) is then subjected to the secondary dehydrohalogenation reaction at the next step (V). The amount of the halogen-removing agent to be used here is determined on the basis of the entire residual halogen content in a crude polyglycidylamino compound produced at the step (II) of the primary dehydrohalogenation reaction. The amount to select is usually in the range from 1 to 2 moles per mole of the entire halogen. Similarly, the amount of the phase transfer catalyst is also determined on the basis of the entire halogen content. The amount to select is in the range from $10^{-4}$ to 2 moles, preferably from $10^{-3}$ to $10^{-1}$ mole, per mole of the residual halogen. Preferably, the secondary dehydrohalogenation reaction at the step (V) is carried out at a temperature not exceeding 70° C., usually at a temperature in the range from 20° to 50° C.

Further, at the step (VI), the reaction mixture from the secondary dehydrohalogenation reaction at the step (V) is subjected to a washing step. The amount of water to be used here may be selected from the range mentioned above, and naturally, the washing effect improves more if the washing is carried out twice or more.

If there is a solvent used at the washing step (IV), the solvent is removed from the resulting reaction mixture. With this removal, the process of this invention is completed to give intended polyglycidylamino compound. The resulting final mixture, polyglycidylamino compound, has a light color, low viscosity and good storage stability, and its residual halogen content is very low. It can be highly valued as a high-quality epoxy resin capable of meeting with severe requirements in the electronics-related fields.

As detailed above, the process of this invention includes the aforementioned steps (I) to (VI) as essential steps in the process for producing a polyglycidylamino compound from diamine and epihalohydrin. Any steps such as filtration step may be inclined in addition as necessary.

It is a known fact to produce a polyglycidylamino compound from diamine and epihalohyddrin, and it is prevailing practice to produce desired polyglycidylamino compounds by subjecting a halohydrin compound obtained from diamine and epihalohydrin to a dehydrohalogenation reaction using alkali, e.g., sodium hydroxide. In fact, however, the conventional process in the above practice has an insurmountable limit in fully reducing the halogen content to be present in the resulting polyglycidylamino compound.

In contrast, in the process of this invention, the dehydrohalogenation reaction mainly of dehydrohalogenation of a halohydrin compound obtained by adding epihalohydrin to diamine can be completed by the use of a halogen-removing agent in the co-presence of the phase transfer catalyst, specifically on the basis of the following actions of these two members, which, it is understood, remarkably reduces the halogen content in the resulting polyglycidylamino compound. That is, the phase transfer catalyst has an action on metal cation of the halogen-removing agent and renders the halogen-removing agent soluble in an organic phase to transfer it to the organic phase. The reactant which has moved to the organic phase rapidly reacts with a halogen-containing substrate to release halogenated metal. Then, again, the phase transfer catalyst acts on the halogen-removing agent to render it soluble in the organic phase. It is thought that such a cycle system makes the phase transfer catalyst exhibit a catalytic function to promote the dehydrohalogenation reaction.

Owing to actions of the halogen-removing agent and the phase transfer catalyst, the dehydrohalogenation reaction can be carried out rapidly under moderate conditions, and it is made possible to reduce the residual halogen content in polyglycidylamino compounds to such a level which could not have been achieved by the conventional technology.

The following Examples illustrate such a specific effect of the process of this invention.

The following Examples and Comparative Examples use separable flasks having a content volume of 2 l and a heater and a temperature-adjustable reactor with a vacuum-sealed stirrer, cooling coil, Dimroth condenser and nitrogen gas-introducing tube.

The "storage property" referred to in Examples and Comparative Examples means an increase ratio in viscosity of a sample when the sample has been heated at 70° C. for 10 days.

EXAMPLE 1

Epichlorohydrin (740 g, 8 moles) and 36 g (2 moles) of water were charged into a reactor, and 136 g (1 mole) of methoxylylene diamine was charged dropwise to the reactor at room temperature in the beginning, over 3.5 hours with nitrogen current (25 ml/min) in the system. The temperature in the reaction system was maintained at 35° C. during the dropwise charging period of time and for 2 hours after the dropwise charging was finished.

Then, 3.6 g (equivalent to 0.008 mole) of an aqueous solution of 50% benzyltriethyl ammonium chloride was added, and thereafter, 375 g (equivalent to 4.5 moles) of an aqueous solution of 48% sodium hydroxide was added dropwise over 30 minutes. Further, the reaction temperature was maintained at 35° C. for 3 hours to carry out the primary dehydrohalogenation reaction.

After the reaction, the precipitated salt was dissolved by adding 480 g (30 moles) of water, and the resulting solution was separated from an oil phase. 240 g (15 moles) of water was newly added to the oil phase to wash it and the resulting water phase was separated. Then, unreacted epichlorohydrin was disilled off from the oil phase under reduced pressure at 90° C.

644 g of (7 moles) of toluene was added to the resulting crude polyglycidyl methaxylylene diamine, and the product was filtrated by the use of a filter paper (No.1). The filtrate was washed twice with 240 g (15 moles) of water. The process analysis of a part of the oil phase showed that the crude polyglycidyl methaxylylene diamine had an entire chlorine content of 6,700 ppm and a hydrolyzable chlorine content of 1,200 ppm.

To the remaining oil phase were added 3.8 g (0.07 mole) of potassium hydroxide as a halogen-removing agent, 12.5 g (0.07 mole) of hexamethyl phosphoric acid triamide as a catalyst and 2.8 g (0.07 mole) of polyethylene glycol (product name "PEG-400"), to carry out the secondary dehydrohalogenation reaction at 35° C. over 2 hours.

Then, the oil phase was washed twice with 240 g (15 moles) of water.

A volatile content containing toluene was distilled off from the resulting oil phase under reduced pressure at a temperature not exceeding 110° C. over 3 hours. After the volatile content was fully removed, the oil phase was filtrated, while it was hot, by using a Kiriyama funnel (40 φ) to give 330 g of polyglycidyl methaxylylene diamine (yield 91.6%).

The produce analysis showed an entire chlorine content of 3,300 ppm, a hydrolyzable chlorine content of 110 ppm, a viscosity of 1,650 mPas (25° C.), a Gardner color scale of 1 and a storage property of 1.3.

The process analysis of the product before the washing step (IV) with water after the primary dehydrohalogenation reaction in the above Example 1 showed an entire chlorine content of 7,300 ppm and a hydrolyzable chlorine content of 1,800 ppm. From a comparison of these data with the process analysis data after the washing step (IV) after the primary dehydrohalogenation reaction, it is clear that the step of washing with water has an effect in reducing the chlorine content.

Comparative Example 1

The procedure of Example 1 was repeated except that benzyltriethyl ammonium chloride was not used at the primary dehydrohalogenation reaction step and that a toluen-added solution was washed twice with water and then a volatile content containing toluene was distiiled off to obtain a final product.

The product analysis showed an entire chlorine content of 7,500 ppm and a hydrolyzable chlorine content of 1,200 ppm. However, it also showed a storage property of 3.3 and a Gardner color scale of 2. In this connection, the product before washing with water had an entire chlorine content of 13,000 ppm and a hydrolyzable chlorine content of 4,400 ppm.

It is seen that the above results are clearly inferior to the results of Example 1.

Comparative Example 2

The procedure of Example 1 was repeated except that the phase transfer catalyst was not used at the primary and secondary dehydrohalogenation reaction steps and that 12 g of sodium hydroxide was used in place of 3.8 g of potassium hydroxide at the secondary dehydrohalogenation reaction step.

The product analysis showed an entire chlorine content of 6,000 ppm and a hydrolyzable chlorine content of 550 ppm, however, it also showed a storage property of 2.1 and a Gardner color scale of 1 to 2. It is seen that the above results are inferior to the results of Example 1.

Comparative Example 3

The procedure of Example 1 was repeated except that, after the primary dehydrohalogenation reaction, a toluene-added solution was washed with water, without subjecting it to the secondary dehydrohalogenation reaction, to distill off a toluene-containing volatile content, and a final product was obtained.

The product analysis showed a hydrolyzable chlorine content of 800 ppm, however, it also showed a storage property of 1.9 and a Gardner color scale of 1. It is seen that the above results are inferior to the results of Example 1.

Comparative Example 4

The procedure of Example 1 was repeated except that the step of washing with water was not carried out after the primary dehydrohalogenation reaction.

The analysis of the final product showed an entire chlorine content of 4,100 ppm, a hydrolyzable chlorine content of 260 ppm, a storage property of 1.6 and a Gardner color scale of 1 to 2.

It is seen that the above results are inferior to the results of Example 1.

EXAMPLE 2

In Example 1, magnesium sulfate was added to a toluene solution phase prior to the secondary dehydrohalogenation reaction to carry out dehydration treatment. The process analysis of an oil phase after the dehydration teratment showed an entire chlorine content of 6,300 ppm and a hydrolyzable chlorine content of 1,600 ppm.

The procedure of Example 1 was repeated by using 7.2 g (0.064 mole) of potassium t-butoxide as a reaction agent, 5.0 g of dimethyl sulfoxide as a phase transfer catalyst and 2.6 g (0.0064 mole) of polyethylene glycol (product name "PEG-400") in the secondary dehydrohalogenation reaction.

The product analysis showed that the resulting polyglycidyl methaxylylene diamine had a viscosity of 2,200 mPas (25° C.), an entire chlorine content of 530 ppm, a hydrolyzable chlorine content of 40 ppm, a storage property of 2.2 and a Gardner color scale of 2 to 3.

EXAMPLES 3–6

Example 1 was repeated except that the phase transfer catalyst at the primary dehydrohalogenation reaction step and the reaction agent and phase transfer catalyst were changed as shown in the following Table 1.

The results of the product analysis are as shown in Table 1.

TABLE 1

| Example | Primary dehydrohalogenation reaction step Catalyst | Secondary dehydrohalogenation reaction step Reaction agent | Catalyst |
|---|---|---|---|
| 3 | 18-c-6 (*) 2.6 g | potassium hydroxide 3.6 g | PEG 2.6 g |
| 4 | PEG(**) 4 g | sodium hydroxide 2 g sodium thiosulfate 4 g | PEG 2 g |
| 5 | TBPC(***) 3 g | potassium acetate 4.4 g | 18-C-6 1.2 g |
| 6 | HMPA(****) 1.4 g | sodium hydroxide 2.8 g | HMPA 14.2 g |

| Example | Hydrolyzable Chlorine (ppm) | Storage property | Color scale |
|---|---|---|---|
| 3 | 150 | 1.7 | 1 |
| 4 | 220 | 1.5 | 1 |
| 5 | 180 | 1.6 | 1 |
| 6 | 170 | 1.5 | 1 |

(*): 18-c-6: 18-crown-6
(**): PEG: polyethylene glycol
(***): TBPC: tetrabutylphosphonium chloride
(****): HMPA: hexamethyl phosphonic acid triamide

What we claim is:

1. In a process for producing a polyglycidylamino compound represented by the general formula (1)

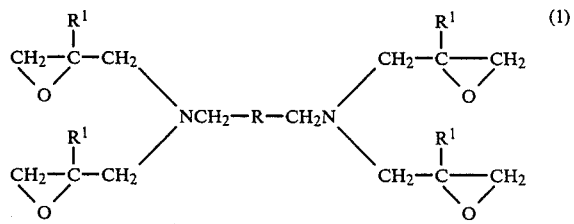

wherein R represents a phenylene group or cyclohexylene group and $R^1$ represents a hydrogen atom or methyl group, by reacting a diamine represented by the general formula (2)

$$H_2NCH_2-R-CH_2NH_2 \quad (2)$$

wherein R is as defined above,
with an epihalohydrin represented by the general formula (3)

wherein $R^1$ is as defined above, and X represents a chlorine or bromine atom,
and then carrying out a dehydrohalogenation reaction of the reaction mixture; the improvement which comprises:
   (I) reacting the diamine with an excess amount, based on the diamine, of an epihalohydrin in the presence of water and at a temperature not to exceed 60° C.,
   (II) conducting a primary dehydrohalogenation reaction step in which the addition reaction mixture obtained in step (I) is reacted with a halogen-removing agent in the co-presence of at least one phase transfer catalyst,
   (III) adding water to the product obtained in step (II), separating an organic phase from an aqueous phase, and distilling off unreacted epihalohydrin from the organic phase, (IV) washing the product obtained in step (III) with water, and (V) subjecting the washed product to a secondary dehydrohalogenation reaction step in which the crude polyglycidylamino compound from step (IV) is reacted with a halogen-removing agent in the co-presence of at least-one phase transfer catalyst, (VI) washing the obtained reaction mixture with water, and recovering the desired polyglycidylamino compound.

2. A process for producing a polyglycidylamino compound according to claim 1 wherein the phase transfer catalyst is at least one selected from the group consisting of:

Group 1: onium salt compounds.

Group 2: macrocyclic polyether compounds selected from the group of crown ethers and cryptands, Group 3: linear polyether compounds selected from the group of polyalkylene oxides and their derivatives having alkyletherified terminals and polyether amines.

Group 4: aprotic polar compounds.

3. A process for producing a polyglycidylamino compound according to claim 1 wherein the halogen-removing agent is at least one member selected from the group consisting of hydroxide of alkali metal, alkali earth metal, inorganic acid salt of alkali metal or alakali earth metal, alkali metal or alkali earth metal salt of aliphatic or aromatic carboxylic acid, alkali metal alkoxide and alkali metal phenoxide.

4. A process for producing a polyglycidylamino compound according to claim 1 wherein the step (I) uses epihalohydrin in an amount of 5.5 to 15 moles per mole of diamine.

5. A process for producing a polyglycidylamino compound according to claim 1 wherein the step (I) uses water in an amount of 0.5 to 15 moles per mole of diamine.

6. A process for producing a polyglycidylamino compound according to claim 1 wherein the amount of the halogen-removing agent used at the step (II) is greater than 4 moles per mole of diamine.

7. A process for producing a polyglycidylamino compound according to claim 1 wherein the step (II) uses the phase transfer catalyst in an amount of $10^{-4}$ to $10^{-1}$ mole per mole of diamine.

8. A process for producing a polyglycidylamino compound according to claim 1 wherein the temperature of the reaction system at the step (II) is not higher than 70° C.

9. A process for producing a polyglycidylamino compound according to claim 1 wherein the reaction mixture is dissolved in an organic solvent before the washing treatment with water at the step (IV).

10. A process for producing a polyglycidylamino compound according to claim 9 wherein the organic solvent is compatible with and inert to the polyglycidylamino compound and is not substantially compatible with water.

11. A process for producing a polyglycidylamino compound according to claim 10 wherein the organic solvent is at least one aromatic hydrocarbon selected from the group consisting of benzene, toluene and xylene.

12. A process for producing a polyglycidylamino compound according to claim 9 wherein the organic solvent is used in an amount of 300 to 500 parts by weight per 100 parts by weight of the polyglycidylamino compound.

13. A process for producing a polyglycidylamino compound according to claim 1 wherein the step (IV) or (VI) uses water in an amount of 10 to 200 parts by weight per 100 parts by weight of reaction mixture.

14. A process for producing a polyglycidylamino compound according to claim 1 wherein the step (V) uses the halogen-removing agent in an amount of 1 to 2 moles per mole of the entire residual halogen content in the crude polyglycidylamino compound obtained at the step (IV).

15. A process for producing a polyglycidylamino compound according to claim 1 wherein the step (V) uses the phase transfer catalyst in an amount of $10^{-4}$ to 2 moles per mole of the entire halogen content in the crude polyglycidylamino compound obtained at the step (VI).

16. A process for producing a polyglycidylamino compound according to claim 1 wherein the temperature of the reaction system at the step (V) is not higher than 70° C.

* * * * *

UNITED STATES PATENT AND TRADEMARK OFFICE
CERTIFICATE OF CORRECTION

PATENT NO.   :   4,871,867
DATED        :   October 3, 1989
INVENTOR(S)  :   TOSHIO HIDAKA and TETSUO MIZUNO It is certified that error appears in the above-identified patent and that said Letters Patent is hereby corrected as shown below:

On the title page, in the ABSTRACT, line 16, change "step (II)" to --step (III)--.

Column 3, line 28, change "(III)" to --(IV)--;
          line 36, change "(IV)" to --(V)--.

Column 4, line 66, delete "solvents";
          line 67, change "vent" to --vents--.

Column 7, line 1, change "inclined" to --included--.

Column 12, line 41 (claim 15, line 6), change "(VI)" to --(IV)--.

Signed and Sealed this

Eleventh Day of June, 1991

*Attest:*

HARRY F. MANBECK, JR.

*Attesting Officer*       *Commissioner of Patents and Trademarks*